United States Patent [19]

Strumia

[11] Patent Number: 4,675,314

[45] Date of Patent: Jun. 23, 1987

[54] THERAPEUTICAL USE OF PHOSPHOCREATINE

[75] Inventor: Ettore Strumia, Turin, Italy

[73] Assignee: Schiapparelli Farmaceutici S.p.A., Milan, Italy

[21] Appl. No.: 847,469

[22] Filed: Apr. 3, 1986

[30] Foreign Application Priority Data

Apr. 17, 1985 [IT] Italy .............................. 20379 A/85

[51] Int. Cl.⁴ ..................... A61K 31/66; A61K 33/06; A61K 33/10; A61K 33/14

[52] U.S. Cl. .................................. 514/75; 424/153; 424/154; 424/156

[58] Field of Search ....................... 424/153, 154, 156; 514/75

[56] References Cited

PUBLICATIONS

Merck Index 7th ed. (1976) p. 956.
Chem. Abst. 85 (1976)—117149b.

Primary Examiner—Stanley J. Friedman
Attorney, Agent, or Firm—Oblon, Fisher, Spivak, McClelland & Maier

[57] ABSTRACT

A solution for infusion to be employed in the treatment of acute myocardial infarction and as a myocardium protecting agent during open heart surgery, containing as the active ingredient an effective amount of phosphocreatine.

5 Claims, No Drawings

THERAPEUTICAL USE OF PHOSPHOCREATINE

BACKGROUND OF THE INVENTION

Phosphocreatine as such or in the form of its alkali metal salts has found pharmacological and therapeutical use in pathologic conditions of striated musculature, such as muscular atrophy and dystrophy, and also of heart musculature, such as myocardiosclerosis, degenerative myocardiopathies and, more generally, anoxies, i.e. those conditions in which the myocardial contractility must be restored as quickly as possible.

The dosages at which phosphocreatine, as such or in the form of its alkali metal salts, diplays said biological properties in animals, for instance in dogs, generally range between about 0.5 mg/kg and about 6 mg/kg.

In therapy, they are administered to patients suffering from the above mentioned pathologic conditions, by intramuscular or intravenous route in a daily dosage ranging between about 200 and about 400 mg. The pharmaceutical preparations contains the active ingredient in an amount of about 200 mg, in combination with the usally employed pharmaceutical carriers.

DISCLOSURE OF THE INVENTION

This invention is concerned with a novel therapeutical use of phosphocreatine, chemically N-(alpha-imino-alpha-phosphonamido)-methyl-N-methylglycine

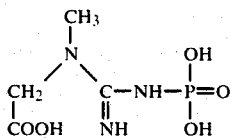

Phosphocreatine is a well known natural substance. It is essentially distributed within several tissues of vertebrates, particular within the skeleton muscles. It was first isolated from frog muscles (Eggleton, Biochem. J. 21, 190, 1927) and cat muscles (Fiske et al., J. Biol. Chem. 81, 629, 1929). Its chemical synthesis by phosphorylation of creatine was first described by Zeile et al., J. Physiol. Chem. 256 193, 1938; Ennor et al. Biochem. J. 43 190, 1948; Ennor et al., Phisiol. Rev. 38 631, 1938. A more recent chemical synthesis is described in Italian Pat. No. 1,044,765.

Phosphocreatine is formed in muscular tissue by phosphorylation of creatine. It has a fundamental role in maintaining a valid muscle contraction, a physico-chemical phenomenon conditioned by energy utilization. It is known that the muscular contraction is caused by the release of a phosphorus molecule by adenosine triphosphate (ATP) which is converted to adenosine diphosphate (ADP).

This latter needs more phosphoric acid in order to regenerate ATP, which therefore represents the energy supply necessary for maintaining the ability of a valid muscle contraction.

Under rest conditions, the regeneration of ATP consumed in basal activity occurs at the expenses of those physiological processes which are in condition to supply phosphoric radicals with high energy contents. These radicals derive from the metabolic breakdown of glycogen contained in muscles.

Under activity conditions the necessary energetic requirement is substantially increased, and becomes insufficient. In these circumstances the ready supply of phosphoric radicals with high energetic level is provided for by the phosphocreatine present in muscle. Phosphocreatine is synthesized through the same metabolic mechanism which leads to the synthesis of ATP (cleavage of glucids with formation of two phosphocreatine moles for each mole of formed lactic acid).

It is apparent that the hexogenic phosphocreatine supply allows to save all or most of the metabolic work of glucid breakdown which, as above pointed out, is necessary to ensure the supply of phosphoric radicals with high potential level both to ATP and to phosphocreatine.

It has been now surprisingly found that phosphocreatine, as such or in the form of its alkali metal salts, when administered at markedly higher dosages than those at which it displays its activity on striated musculature, exerts a stabilizing action on the sarcolemmatic membrane of myocardial cells, with a protective activity of that membrane, if used in cardioplegic solutions during cardiac surgery or infusion in acute myocardial ischemia.

On a practical basis, the best results are obtained by employing in cardiac surgery phosphocreatine solutions having concentrations in the range of about 10 mmole per liter and in acute myocardial ischemia, phosphocreatine solutions having concentration in the range between 100 mmole and about 800 mmole/liter.

As a preferred embodiment of the invention, the clinical treatment in acute myocardical ischemia is carried out by first parenterally administering to patients a solution containing from about 490 to about 980 mmole/liter of phosphocreatine as such or in the form of an alkali metal salt thereof, followed by a second solution by infusion containing from about 200 to about 800 mmole/liter of phosphocreatine as such or in the form of an alkali metal salt thereof; in cardiac surgery using cardioplegic solutions containing phosphocreatine 10 mmole/liter.

During investigations carried out in recent years it come out that, by using higher dosages with respect to those formerly employed, phospocreatine displays additional mechanisms beyond the so far suggested intervention in the Lohmann reaction.

Studies of electronic microscopy carried out using colloidal lanthanum as a tracer, both in humans and animals, showed a marked stabilization of the sarcolemma of ischemic cardiomyocytes.

Colloidal lanthanum, ultrastructural marker of early sarcolemma injury, does not penetrate normal cardiac cells and accumulates within the intracellular space. Under ischemic conditions, on the contrary, the sarcolemma of cardiomyocytes become permeable to colloidal lanthanum which may easily be put into evidence with ultrastructural studies connected with mitocondrial membranes.

In the presence of 10 mM concentrations of phosphocreatine the sarcolemma of cardiomyocytes remains non-permeable to colloidal lanthanum also under conditions of severe experimental ischemia, thus showing a protective effect of the substance on the integrity of the cellular membrane of ischemic cardiomyocytes.

This effect was always observed in experiments carried out with different experimental procedures: experimental infarction from coronary ligation in rabbits and dogs, complete ischemia of papillar muscle slices of mini-pig in vitro, heart surgery interventions in man.

To similar conclusions leads also the examination of other direct and indirect indexes of integrity of the cellular membrane, such as the ultrastructural morphological study and enzymatic assays (CPK release).

The importance of this observation becomes apparent if it is considered that sarcolemma is the most sensitive cardiac cell structure and the first to undergo alterations under ischemic conditions.

To protect the sarcolemma from ischemic injury means therefore to prevent a series of events leading to irreversible cellular injury, with undesirable effects on the metabolism of myocardium, its morphological integrity, its contractile function, its electrophysiology.

Just on the basis of these considerations it is appropriate to interpret the effects of phosphocreatine observed in the various experiments in vitro and in vivo on animals and humans, which are unanimously referred to in terms of better morphologic, biochemical, functional (contractile capacity) and electric (less incidence of arrhytmias) recovery.

An interpretation on biochemical basis of this membrane stabilizing effect was suggested during studies on the metabolism of membrane phospholipids in cardiomyocytes of the heart of dogs subjected to coronary ligation.

Basing on the results of these studies it was concluded that the membrane stabilizing effect by phosphocreatine might be, at least partially, attributed to on inhibitory action on the breakdown of the phospholipids of the cell membrane of cardiomyocytes which, under ischemic conditions, are normally degraded to lysophosphatids.

Furthermore, by the same experiments, a direct binding of phosphocreatine to the sarcolemma of cardiomyocytes is confirmed by specific studies of "ligand binding".

In order to illustrate the results obtained with phosphocreatine in the treatment of patients subjected to open heart surgery or clinically treated for myocardic infarction, examples are given hereinafter of the cardioplegic solution used for infusion and of the studies carried out with the use of said solution.

EXAMPLE I

Cardioplegic solutions are prepared, both with and without the addition of phosphocreatine, in such a way as to obtain a final one liter volume, to be diluted with 500 ml of blood containing 5,000 heparine units before the use in patients. The solutions have the following final concentrations and physical properties:

| Components and properties | Control solution | Phosphocreatine solution |
| --- | --- | --- |
| $K^+$ | 16.0–25.0 mM | 16.0–25.0 mmole |
| $Na^+$ | 50.0 mM | — |
| $Ca^{2+}$ | 0.75–1.2 mM | 0.75–1.2 mmole |
| $Mg^{2+}$ | 0–16.0 mM | 0–16.0 mmole |
| $Na_2$ phosphocreatine | — | –10.0 mmole |
| pH | 7.9–8.0 | 7.9–8.0 |
| Osmolarity | 340–360 | 340–360 |

EXAMPLE II

Replacement of cardiac valves was effected on 29 subjects having on age comprised between 20 and 51 years. In 22 cases the valvular injuries had rheumatic origin, in 7 cases they were caused by infectious endocarditis.

To carry out the intervention, the aorta was ligated for periods ranging between 42 and 138 minutes (overage: 79 minutes). To protect the heart during the intervention cardioplegic solutions with and without addition of phsphocreatine were used. The solutions were prepared immediately before the intervention and introduced, after oxygenation and cooling to 6°–8° C., into the coronaries or at the root of the aorta just after ligation, in an amount of 400–500 ml, and then, every 20–25 minutes, of additional 400–500 under a pressure of 40–50 mm Hg.

The phosphocreatine solution was employed on 16 out of the 29 treated subjects.

After release of the aortic clamp at the end of the interventions, marked differences were noted between the two groups of patients. In the control group, one or more defibrillations were necessary in 8 of the 13 cases, while in the group treated with phosphocreatine defribillation was necessary only in 1 of the 16 patients. The recovery of cardiac activity was usually associated with transitional disturbances of the atrioventricular and intraventricular conduction which, however, quickly disappeared in the group treated with phosphocreatine. In this group, the sinus rhythmus, was more frequently restabilized, and the recovery time necessary for stabilizing circulation and ECG after liberation of the aorta was markedly shorter, as an average 16 minutes instead of 27 minutes for controls.

EXAMPLE III

Experiments were carried out on 60 patients from acute myocardial infarction, hospitalized within 6 hours after the beginning of the symptoms.

Treatment was carried out according to the following schedule:

| First day: | | |
| --- | --- | --- |
| parenteral administration: | phosphocreatine | 2 g in 8–16 ml |
| intravenous infusion using the solution of Example 1 during the following 2 hrs | " | 2 g |
| intravenous infusion as above during the following 20–22 hours | " | 4 g |
| From the 2nd through the 7th day: | | |
| parental administration: | 2 g twice a day of phosphocreatine | |

The clinical checking of patients included precordial mapping, Holter monitoring, decrease in frequency of heart failure.

Treatment with phosphocreatine caused a statistically significant decrease of the total elevation of ST segment and to a decrease in frequency of development of cardiac arrhythmias. In 33 percent of the treated cases heart congestion was observed, but this percentage increased to 56 per cent in a group of untreated patients.

Mortality was 10 percent in treated patients, and increased to 16 percent in untreated patients. These differences in percentage are statistically significant.

I claim:

1. A method for treating heart infarction and for protecting myocardium during the surgical open heart intervention, which consists in administering to humans a solution containing an effective amount of a compound selected from phosphocreatine and an alkali metal salt thereof.

2. A method of treating heart ischemia and infarction according to claim 1, comprising administering to humans a first solution for parenteral administration containing from about 0.5 to about 2.5 mole/liter of a compund selected from phosphocreatine and an alkali metal salt thereof, and administering a second solution for infusional administration containing from about 5 to about 50 mmole/liter of a compound selected from phosphocreatine and an alkali metal salt thereof.

3. A method for protecting myocardium during surgical open heart interventions according to claim 1, comprising administering a cardioplegic solution containing from about 3 to about 35 mmoles/liter of a compound selected from phosphocreatine and an alkali metal salt thereof.

4. A solution for infusion to be used in the treatment of heart ischemia and infarction, having the following compositions:

disodium phosphocreatine: 3.0–35.0 mmole/l
$K^+$ ions: 16.0–25.0 mmole/l
$Ca^{++}$ ions: 0.75–1.2 mmole/l
$Mg^{++}$ ions: 0–16 mmole/l
Sterile distilled water q.s. to 1,000 ml.

5. A solution as claimed in claim 4, in which the concentration of disodium phosphocreatine is 8–10 mmole/liter.

* * * * *